United States Patent [19]

Fahmy

[11] Patent Number: 4,532,235
[45] Date of Patent: Jul. 30, 1985

[54] O-ETHYL S-PROPYL S-S-BUTYL PHOSPHORODITHIOATE

[75] Inventor: Mohamed A. H. Fahmy, Princeton, N.J.

[73] Assignee: FMC Corporation, Philadelphia, Pa.

[21] Appl. No.: 561,424

[22] Filed: Dec. 14, 1983

Related U.S. Application Data

[60] Division of Ser. No. 470,736, Feb. 28, 1983, abandoned, which is a continuation-in-part of Ser. No. 297,437, Aug. 28, 1981, abandoned.

[51] Int. Cl.$^3$ .................... A01N 57/12; C07F 9/165
[52] U.S. Cl. .................................... 514/144; 260/963
[58] Field of Search .................. 260/963; 424/224

[56] References Cited

U.S. PATENT DOCUMENTS

| | | | |
|---|---|---|---|
| 2,822,374 | 2/1958 | Vogel | 260/963 |
| 3,839,510 | 10/1974 | Kudamatsu et al. | 260/963 |
| 4,273,769 | 6/1981 | Koyanagi et al. | 260/963 |
| 4,383,991 | 5/1983 | Gough | 424/224 |

FOREIGN PATENT DOCUMENTS 29847 12/1969 Japan.
1081270 8/1967 United Kingdom.

*Primary Examiner*—Anton H. Sutto
*Attorney, Agent, or Firm*—Robert L. Andersen; H. Robinson Ertelt

[57] ABSTRACT

An O-ethyl S,S-dialkyl phosphorodithioate of the formula:

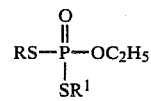

in which one of R and R$^1$ is an s-butyl group and the other of R and R$^1$ is n-propyl, exhibiting high levels of activity against soil borne insects and nematodes and low phytotoxicity, is described and exemplified.

3 Claims, No Drawings

O-ETHYL S-PROPYL S-S-BUTYL PHOSPHORODITHIOATE

This application is a divisional of U.S. patent application Ser. No. 470,736 filed Feb. 28, 1983, which is a continuation-in-part of U.S. application Ser. No. 297,437 filed Aug. 28, 1981, both now abandoned.

The present invention relates to pesticidal compounds which are O-ethyl S,S-dialkyl phosphorodithioates, in particular to one in which one of the S-alkyl groups is an s-butyl group and the other is an n-propyl group. The compound of this invention exhibits uniquely high levels of control of both soil borne insects and nematodes, low phytotoxicity, and excellent residual activity when incorporated into the soil in which agricultural crops are or are about to be planted.

Agricultural chemicals normally used in the control of soil insects and nematodes suffer the disadvantages that they are either (1) highly active against soil insects but low in nematicidal action or (2) highly nematicidal but much less active against soil insects.

Also, agricultural practices necessitate application of soil pesticides as a single application at the beginning of the planting season to protect the roots of the plants from insects and nematodes throughout the growing period. In particular the root damaging stages of insects, for example corn rootworm larvae, will appear several weeks after planting time. Therefore it is important that soil chemicals exhibit long residual action and be of low phytotoxicity during the growing period of plants. For this reason soil pesticides having short residual activity are undesirable.

These disadvantages have resulted in the application of two chemicals, one as an insecticide and the other as a nematicide, or the use of high application rates of one chemical to overcome poor insecticidal activity, poor nematicidal activity, or short residual activity of that chemical.

U.S. Pat. No. 3,112,244 discloses compounds of the formula:

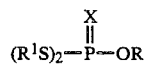

in which X is oxygen or sulfur and each R is a lower alkyl group, but does not disclose compounds in which $R^1$ is α-branched. The compounds of this patent are used for control of nematodes, but have low residual soil insect and nematicidal activity.

Japanese Patent Publication No. 29847/1969, published Dec. 3, 1969, relates to a process for preparing certain dithiophosphate esters said to have strong fungicidal, insecticidal, acaricidal, and nematicidal activities. This publication discloses, inter alia, compounds of the general formula

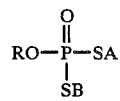

In one specific embodiment R is ethyl and A and B are each t-butyl. In another R is ethyl, one of A and B is s-butyl, the other of A and B is n-butyl. While each of these compounds is highly active against nematodes or against soil borne insects, neither is highly active against both groups of crop pests.

The present invention provides a compound having the desired combination of properties, namely long soil residual insecticidal activity, high nematicidal activity, and low phytotoxicity. The compound having these properties is an O-ethyl S,S-dialkyl phosphorodithioate having the formula:

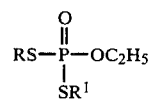

in which one of R and $R^1$ is s-butyl and the other of R and $R^1$ is n-propyl.

This compound is highly active against both pest groups at extremely low application rates. It also exhibits unexpectedly high residual activity against soil borne insects and nematodes at low application rates, and is without any substantial phytotoxic effect at normal use levels. The combination of all these desirable features in a single compound is highly unexpected.

The compound of this invention may be prepared by reacting S-alkyl phosphorothioic dichloride (II) with ethanol to produce an O-ethyl S-alkyl phosphorothioic chloride (III) in accordance with the general reaction:

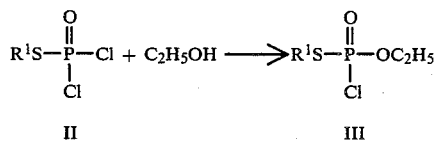

then reacting III with a basic salt, for example an alkali metal or alkaline earth metal salt, of an alkanethiol to produce the compound of this invention, in accordance with the general reaction

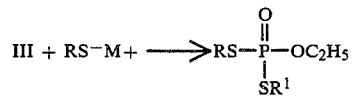

Another method for preparing the compound of this invention is by reacting an alkanesulfenyl chloride with a diethyl chlorophosphite to produce III (K. A. Petrov et al., Zh. Obsheh. Khim. 26, 3381–4 1956), then reacting that with an alkanethiol salt as shown above.

The following example illustrates preparation of the compound of the invention.

EXAMPLE 1

Synthesis of O-Ethyl S-propyl S-s-butyl phosphorodithioate

To a solution of 76.2 g (1.0 mole) of 1-propanethiol in 300 ml of toluene, maintained between −3° C. and 7° C., 148 g (1.1 mole) of sulfuryl chloride was added dropwise during a one hour period. To this mixture at −3° C. was added 60.1 g (1.0 mole) glacial acetic acid in one portion. The dropwise addition of 137.3 g (1.0 mole) of phosphorous trichloride at −3° to 6° C. followed during a one hour period. The reaction mixture was then stirred at room temperature for approximately sixteen hours. After adding 3 ml of sulfuryl chloride the solvent was removed using a rotary evaporator under vacuum. The residue was vacuum distilled, yielding 155.9 g of S-propyl phosphorothioic dichloride, b.p. 72°–73° C./2 mm of Hg.

To a solution of 40 g (0.20 mole) of S-propyl phosphorothioic dichloride in 250 ml of toluene cooled wih an iced salt water bath was added dropwise 11.5 g (0.25 mole) of ethanol followed by 16.4 g (0.20 mole) of pyridine. This mixture was stirred at room temperature for 16 hours. The pyridine hydrochloride was filtered off and the solvent removed using a rotary evaporator under vacuum. The yellow oil that remained was vacuum distilled, yielding 28.05 g of O-ethyl S-propyl phosphorothioic chloride, b.p. 81°–84° C./0.25 mm of Hg.

To a suspension of 1.2 g (0.05 mole) of sodium hydride in 100 ml of dry tetrahydrofuran cooled with an ice water bath was added 4.4 g (0.05 mole) of 1-methyl-1-propanethiol dropwise under a nitrogen atmosphere. This mixture was stirred for approximately 0.5 hour. After cooling the reaction mixture in an ice water bath 10.1 g (0.05 mole) of O-ethyl S-propyl phosphorothioic chloride was added rapidly and the mixture allowed to stand for approximately 16 hours. The solvent was removed using a rotary evaporator under vacuum. Toluene (100 ml) was added to the residue. This solution was washed twice with 50 ml portions of water, dried over anhydrous sodium sulfate, filtered, and stripped of solvent, leaving a residue. This residue was distilled under vacuum, yielding 5.0 g of O-ethyl S-propyl S-s-butyl phosphorodithioate, b.p. 75° C./0.05 mm of Hg. The product was redistilled at 80°–82° C./0.1 mm Hg. The proton and $^{31}$P nmr spectra of this product were consistent with the assigned structure.

The compound of this invention is preferably used to control nematodes and soil borne insects such as corn rootworm, but may also control some insects which feed on the above ground portions of the plant. For nematode and corn rootworm control the compound is advantageously applied to or incorporated into the soil in which crops are planted or are to be planted, or to the plant's roots. If it is desired to control only pests attacking the above ground portions of the plant, some of the compounds of the invention are highly active toward selected insects and may suitably be applied to the above ground portion of the plant.

The compound is generally not applied full strength but is typically applied as a formulation which may be applied as such or further diluted for application. Typical formulations include compositions of the active ingredient in combination with one or more agriculturally acceptable adjuvants, carriers or extenders, preferably with a surface active agent, and optionally with other active ingredients. Suitable formulations include granules, powders, or liquids, the choice varying with the type of pest and environmental factors present at the particular locus of infestation. Thus, the compound may be formulated as granules of various sizes, as dusts, as wettable powders, as emulsifiable concentrates, as solutions, as dispersions, as controlled release compositions, and the like. A typical formulation may vary widely in concentration of active ingredient depending upon the particular agent used, the additives and carriers used, other active ingredients, and the desired mode of application.

With due condideration to these factors the active ingredient of a typical formulation may, for example, be suitably present at a concentration of about 0.01% up to about 95%, preferably 0.1% up to 90%, of the formulation, agriculturally acceptable carriers, diluents, adjuvants, and other suitable active ingredients comprising the balance of the formulation. Compatible surface active agents, if employed in a formulation, may be present at various concentrations, suitably in the range of 1 to 30% by weight of the formulation.

The formulation may be used as such or diluted to a desired use dilution with a diluent or carrier suitable for facilitating dispersion of the active ingredients. A suitable concentration of the active ingredient in the use dilution may be in the range of 0.005% to 10%, more preferably 0.01% to about 10%, by weight.

Many variations of spraying, dusting, and controlled or slow release compositions of a type known in the art may be used by substituting or adding the insecticidal compound of this invention into the compositions known or apparent to the art.

The insecticidal compound of this invention may be formulated and applied with other compatible active agents including nematicides, insecticides, acaracides, fungicides, plant regulators, herbicides, fertilizers, and the like.

In applying the compound, whether alone or with other agricultural chemicals, an effective insecticidal amount of the active ingredient must be applied. While the application rate will vary widely depending on the choice of compound, formulation, mode of application, plant species being protected, planting density, and other like factors, a suitable use rate for agricultural crops may be in the range of 0.005 to 3 kg/ha, preferably 0.01 to about 1 kg/ha.

The compound of this invention was tested for activity as described below.

Soil Incorporation Tests for Residual Southern Corn Rootworm Control

A solution of the test compound, containing 335 ppm test compound in 100 ml of a solution containing 90% water, 9.75% acetone and 0.25% octylphenoxypolyethoxyethanol, was stirred into topsoil in an amount sufficient to provide the desired concentration. The container for the test sample was capped and stored for 42 days. At the end of the storage period each test sample was infested with 10 larvae and a kernel of germinating corn as a food supply. The samples were then recapped and returned to storage for three days at which time the tests were read for percent mortality.

The soil samples may have varied from test to test. No attempt was made to distinguish between soil types.

The residual activity of the compound of this invention is reported in the Table below. The compound of the invention showed excellent residual activity against the Corn Rootworm. Included in the test for comparative purposes were compounds designated A through D. Compound A is O-ethyl S-s-butyl S-n-butyl phosphorodithioate. Compound B is O-ethyl S,S-di-t-butyl phosphorodithioate. Compound C is O-ethyl S,S-dipropyl phosphorodithioate. Compound D is O-ethyl S-t-butyl S-n-propyl phosphorodithioate. The compound of the invention was considerably more effective against corn rootworm than compounds A through D.

Soil Incorporation Tests for Nematode Control and Phytotoxicity

Each compound was tested for nematicidal activity as a formulated material. The formulation used was a standard 5 wt. % dust formulation made up as follows:
Active ingredient (100% active basis)—5 parts Base—95 parts
  96%—attaclay
  2%—highly purified sodium lignosulfonate (100%)
  2%—powdered sodium alkylnaphthalenesulfonate (75%)

The mixture was ground to a fine powder.

The formulation described above was tested for activity against root-knot nematode (*Meloidogyne incognita*) as follows:

Nematode Culture—Tomato seedlings with two large true leaves were transplanted into six inch clay pots containing steam-sterilized sandy soil. One week after transplanting, galled roots of nematode-infested tomato plants, with fully developed egg masses, were placed in three holes in the soil around the seedling roots. Holes were then closed with soil. The plants were allowed to grow until fully developed egg masses were formed (6 to 7 weeks after inoculation).

Inoculum Preparation—Infected tomato roots, containing egg masses, were cleaned under running tap water, cut into short pieces and comminuted with water in an electrical blender for 30 seconds. The shredded roots were poured onto layers of washed sand in a fiberglass flat. The flat was covered with plastic sheeting and kept at greenhouse temperatures for 3 to 7 days to allow about 50% of the larvae to hatch.

Preparation of Root-Knot Nematode Infested Soil—Samples of the infested soil prepared as described above were processed for nematodes by using the Caveness and Jensen centrifugal-sugar flotation extraction technique [Caveness, F. E. and Jensen, H. J., "Modification of the Centrifugal Flotation Technique for the Isolation and Concentration of Nematodes and their Eggs from Soil and Plant Tissue," Proc. Helm. Soc., Washington, 22, 87–89 (1955).]

A 500 mesh sieve was used to collect the nematodes and eggs, and their number was estimated under a stereomicroscope. Enough sand containing eggs and larvae was mixed with additional steam-sterilized sandy soil so that there were 800 to 1000 root-knot nematode larvae and eggs per pot of soil (three inch diameter each, containing approximately 300 g soil). Depending on the total amount of nematode infested soil needed, mixing was accomplished by use of a cement mixer for 5 minutes or the V-shaped rotary mixer for 60 seconds.

Soil so infected was used for soil incorporated nematicidal studies within two days of preparation. The formulated compounds to be tested for nematicidal activity were incorporated in the root-knot nematode infested potting soil to give soil treatment at several application rates in the range of 2.5 to 25 ppm (weight chemical/weight soil). Young tomato plants were planted in this soil in three inch pots. Two weeks after planting the roots of all plants were examined and rated in comparison to untreated checks, which were treated in the same manner as those treated with the active ingredient. Compounds A through D, supra, were also included for comparison.

The results of the tests against Rootknot nematode are shown in the Table below. High levels of initial nematode control were obtained by the compound of the invention and by Compound D. Compound B exhibited poor nematode control. Compounds B and D provided no control in the Residual test, whereas the compound of the invention provided 95% control. The level of observed phytotoxicity in the Initial and Residual nematode tests was slight to none for all compounds tested.

TABLE

| | Soil Incorporation Tests | | | |
| | Percent Control | | | |
| Compound | Residual[1] SCR | Initial[2] Nematode | Residual[3] Nematode | Phyto[4] Toxicity |
|---|---|---|---|---|
| Example 1 | 100 | 100 | 95 | 1 |
| A | 10 | 100 | | |
| B | 65 | 35 | 0 | |
| C | 5 | 85[5] | | |
| D | 75 | 98 | 0 | 1+ |

[1] SCR = Southern corn rootworm (*Diabrotica undecempunctata howardi* Barber). At 1 ppm (wt active ingredient/weight soil)
[2] All results at 10 ppm (weight active ingredient/weight soil) 14 days after treatment and planting
[3] All results at 15 ppm (weight active ingredient/weight soil) 8 weeks after treatment, 2 weeks after planting
[4] 0 = no injury; 1 = slight; 2 = moderate; 3 = severe; 4 = plant not expected to survive. Average of all concentrations tested.
[5] Tested as a 10% granular formulation. Average of 5 tests.

I claim:

1. A compound of the formula

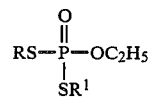

in which one R and $R^1$ is s-butyl and the other R and $R^1$ is n-propyl.

2. An insecticidal or nematicidal composition comprising an insecticidal or nematicidal amount of the compound of claim 1 in admixture with at least one agriculturally acceptable diluent, carrier, or adjuvant.

3. A method for controlling soil borne insects and nematodes which comprises applying to the soil in which agricultural crops are planted or are to be planted an insecticidal and nematicidal amount of the compound of claim 1.

* * * * *